(12) United States Patent

Zhang et al.

(10) Patent No.: US 10,571,598 B2
(45) Date of Patent: Feb. 25, 2020

(54) SECURITY INSPECTION APPARATUS AND METHOD

(71) Applicant: Nuctech Company Limited, Beijing (CN)

(72) Inventors: Jianhong Zhang, Beijing (CN); Nei Yang, Beijing (CN); Hongqiu Wang, Beijing (CN); Yumin Yi, Beijing (CN); Hu Tang, Beijing (CN); Guohua Wei, Beijing (CN)

(73) Assignee: Nuctech Company Limited, Beijing (CN)

( * ) Notice: Subject to any disclaimer, the term of this patent is extended or adjusted under 35 U.S.C. 154(b) by 259 days.

(21) Appl. No.: 15/826,530

(22) Filed: Nov. 29, 2017

(65) Prior Publication Data

US 2018/0180761 A1 Jun. 28, 2018

(30) Foreign Application Priority Data

Dec. 23, 2016 (CN) .......................... 2016 1 1208515

(51) Int. Cl.
*G01J 3/44* (2006.01)
*G01V 5/00* (2006.01)
(Continued)

(52) U.S. Cl.
CPC ........... *G01V 5/0033* (2013.01); *G01N 21/65* (2013.01); *G01N 23/046* (2013.01); *G01N 2223/1006* (2013.01); *G01N 2223/419* (2013.01)

(58) Field of Classification Search
CPC .. G01V 5/0016; G01V 5/0008; G01V 5/0066; G01V 5/005; G01V 5/0025; G01V 5/0075; G01V 5/0091; G01N 5/00
See application file for complete search history.

(56) References Cited

U.S. PATENT DOCUMENTS

| 5,642,393 A | 6/1997 | Krug et al. |
| 9,250,180 B2 | 2/2016 | Chen et al. |

(Continued)

FOREIGN PATENT DOCUMENTS

| CN | 104335032 A | 2/2015 |
| CN | 104375203 A | 2/2015 |

(Continued)

OTHER PUBLICATIONS

Office action dated Oct. 31, 2018 for Chinese Application No. 201611208515.6, which corresponds in priority to above-identified subject U.S. Application.

(Continued)

*Primary Examiner* — Don K Wong
(74) *Attorney, Agent, or Firm* — Knobbe, Martens, Olson & Bear, LLP (57) ABSTRACT

A security inspection apparatus and a security inspection method are disclosed. In one aspect, an example apparatus includes a CT inspection device and a Raman spectrum inspection device, the CT inspection device includes: a CT scanner scanning an object to be inspected to generate a CT image, an image recognizing device recognizing the CT image to check whether or not the object has a suspected hazardous article, and an object marking device making a predetermined marker on the object which has the suspected hazardous article. The Raman spectrum inspection device includes: a Raman spectrum measuring device extracting a Raman spectrum of the suspected hazardous article in the object, a Raman spectrum comparing device comparing the Raman spectrum of the suspected hazardous article with Raman spectra of known compositions to determine a composition of the suspected hazardous article, and an object marker recognizing device recognizing the predetermined marker on the object.

16 Claims, 4 Drawing Sheets

(51) Int. Cl.
*G01N 21/65* (2006.01)
*G01N 23/046* (2018.01)

(56) References Cited

U.S. PATENT DOCUMENTS

| | | | |
|---|---|---|---|
| 2004/0051867 A1* | 3/2004 | Brestel | G01J 3/2889 356/318 |
| 2006/0056586 A1 | 3/2006 | Uetake et al. | |
| 2006/0104414 A1 | 5/2006 | Mayo | |
| 2015/0085278 A1 | 3/2015 | Chen et al. | |

FOREIGN PATENT DOCUMENTS

| | | |
|---|---|---|
| CN | 104458693 A | 3/2015 |
| CN | 104865279 A | 8/2015 |
| CN | 105068135 A | 11/2015 |
| CN | 105549119 A | 5/2016 |
| CN | 20627312 U | 6/2017 |
| EP | 2 902 811 A1 | 8/2015 |

OTHER PUBLICATIONS

Office Action Issued for Chinese Application No. 201611208515.6 dated Mar. 23, 2018, and from which priority is claimed by subject U.S. Appl. No. 15/826,530 (in 6 pages).
Extended European Search Report for Application No. 17204813.4 dated Jun. 7, 2018, in 10 pages, which corresponds in priority to the above-identified U.S. application.

* cited by examiner

Fig. 4

SECURITY INSPECTION APPARATUS AND METHOD

CROSS-REFERENCE TO RELATED APPLICATION

This application claims priority to Chinese Patent Application No. 201611208515.6, filed on Dec. 23, 2016, which is hereby incorporated by reference in its entirety for all purposes.

BACKGROUND OF THE DISCLOSED TECHNOLOGY

Field of the Technology

Embodiments of the disclosed technology generally relate to a technical field of security inspection, and in particular to security inspection apparatus and method.

Description of the Related Technology

Currently, methods for performing security inspection on luggage articles mainly include a chemical method (such as ion migration), an electromagnetic method, a neutron method and a ray method. In these methods, an X-ray method is applied most widely. The X-ray method includes two categories, in the first category, the X-ray is used to perform a two dimensional scanning; in the second category, the X-ray CT technology is used.

By using computed tomography (CT) technology to inspect an object, the density information and atomic number information of the object can be determined. As the speed of CT security inspection increases continuously, the application of this technology becomes more and more broad.

However, the CT technology only can recognize suspected articles in the luggage, and cannot determine the specific type of matters of the suspected articles. For example, drugs in the luggage may be recognized by CT technology, but the specific types of the drugs cannot be identified by the technology.

For this circumstance, it needs to send the suspected articles to the professional lab for further analysis. It is very inconvenient for the security inspection because it cannot process the suspected articles in field at the earliest time.

SUMMARY OF THE DISCLOSURE

An embodiment of the disclosed technology provides a security inspection apparatus, including: a CT inspection device and a Raman spectrum inspection device, wherein the CT inspection device includes: a CT scanner arranged to scan an object to be inspected to generate a CT image; an image recognizing device arranged to recognize the CT image to check whether or not the object has a suspected hazardous article; and an object marking device arranged to make (e.g., place) a predetermined marker on the object which has the suspected hazardous article; and wherein the Raman spectrum inspection device includes: a Raman spectrum measuring device arranged to extract a Raman spectrum of the suspected hazardous article in the object, a Raman spectrum comparing device arranged to compare the Raman spectrum of the suspected hazardous article with Raman spectra of known compositions to determine a composition of the suspected hazardous article; and an object marker recognizing device arranged to recognize the predetermined marker on the object.

An embodiment of the disclosed technology provides a security inspection method including: scanning an object to be inspected by using a CT scanner to generate a CT image and checking whether or not the object has a suspected hazardous article; making a predetermined marker on the object having the suspected hazardous article; recognizing the predetermined marker on the object; and extracting a Raman spectrum of the suspected hazardous article in the object which has the predetermined marker and comparing the Raman spectrum of the suspected hazardous article with Raman spectra of known compositions to determine a composition of the suspected hazardous article.

BRIEF DESCRIPTION OF THE DRAWINGS

In order to understand the disclosed technology more clearly, embodiments of the disclosed technology will be described with reference to the following drawings.

In drawings, all of circuits or structures of the embodiments are not shown. Same reference numerals represent same or similar parts or features throughout all of drawings.

DETAILED DESCRIPTION OF CERTAIN ILLUSTRATIVE EMBODIMENTS

Technical solutions of the disclosed technology will be described hereinafter in more detail by the way of embodiments with reference to the attached drawings. The same or similar reference numerals refer to the same or similar elements throughout the description. The explanation to the embodiments of the disclosed technology with referring to the accompanying drawings is intended to interpret the general concept of the disclosed technology, rather than being construed as a limiting to the disclosed technology.

In accordance with a general concept of the disclosed technology, it provides a security inspection apparatus, including: a CT inspection device arranged to scan an object to be inspected to generate a CT image and check whether the object has a suspected hazardous article; and a Raman spectrum inspection device arranged to extract the Raman spectrum of the suspected hazardous article in the object and compare the Raman spectrum of the suspected hazardous article with Raman spectrum of known compositions to determine composition of the suspected hazardous article, wherein the CT inspection device includes: an object marking device arranged to make a predetermined marker on the object which has the suspected hazardous article; and the Raman spectrum inspection device includes: an object marker recognizing device arranged to recognize the predetermined marker in the object.

In addition, in the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
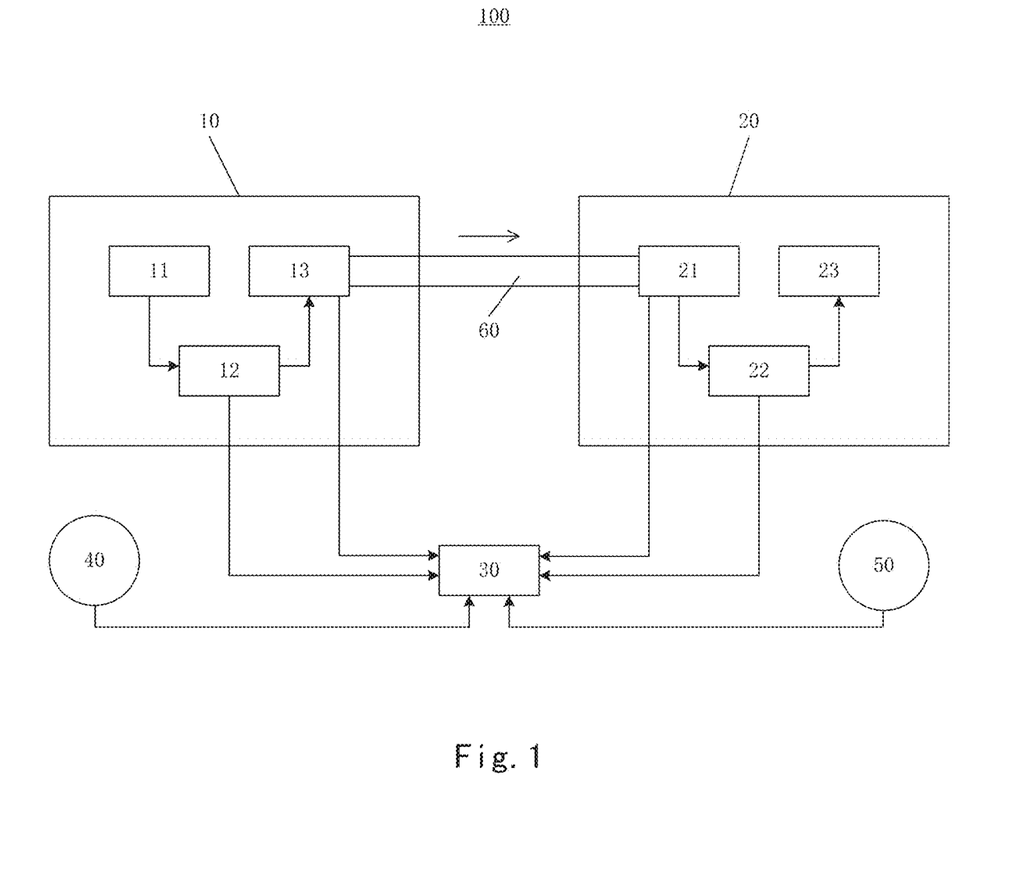
FIG. 1 is a schematic view showing a security inspection apparatus according to an embodiment of the disclosed technology.

FIG. 1 is a schematic view showing a structure of a security inspection apparatus 100 according to an embodiment of the disclosed technology. The security inspection apparatus 100 includes a CT inspection device 10 and a Raman spectrum inspection device 20. In an example shown in FIG. 1, the CT inspection device 10 includes a CT scanner 11, an image recognizing device 12 and an object marking device 13. The CT scanner 11 is arranged to scan an object to be inspected to generate a CT image. The image recognizing device 12 is arranged to recognize the CT image to check whether the object has a suspected hazardous article. The object marking device 13 is arranged to make a predetermined marker on the object which has the suspected hazardous article. The Raman spectrum inspection device 20 may for example include: a Raman spectrum measuring device 21, a Raman spectrum comparing device 22 and an object marker recognizing device 23. The Raman spectrum measuring device 21 is arranged to extract a Raman spectrum of the suspected hazardous article in the object. The Raman spectrum comparing device 22 is arranged to compare the Raman spectrum of the suspected hazardous article with Raman spectrum of known compositions to determine composition(s) of the suspected hazardous article. The object marker recognizing device 23 is arranged to recognize the predetermined marker on the object.

By means of the security inspection apparatus integrated with the CT inspection device and the Raman spectrum inspection device according to an embodiment of the disclosed technology, the defect of the CT inspection device in difficulty of determining the specific compositions of the suspected hazardous articles (for example, drugs, explosives, Inflammable and explosive substance) may be removed such that the object can be inspected more accurately and fast. It is in particular beneficial to inspection of luggage and packs at such as airports, rail stations or the like.

When it has determined the object has the suspected hazardous articles by recognizing and analyzing the CT image and it needs to further inspect the compositions of the suspected hazardous articles in the object, the object marking device 13 may make the predetermined marker on the object which has the suspected hazardous articles to associate the object with its CT image. The object marker recognizing device 23 in the Raman spectrum measuring device 20 may recognize the predetermined marker on the object. On one hand, it may prevent the Raman spectrum measuring device 20 from inspecting the object that has been determined to be safe by the CT inspection device 10 in error to reduce the inspection efficiency; on the other hand, it may associate the compositions of the suspected hazardous articles determined by the Raman spectrum measuring device 20 with the object to ensure correspondence between the inspection results based on the CT image with the inspection results based on the Raman spectrum.

As an example, the object marking device may be a two dimensional code generator, the marker may be a two dimensional code, and the object marker recognizing device may be a two dimensional code recognizing device. The two dimensional code has advantages of large information capacity and strong fault tolerance. However, for example, other manners such as bar codes may also be used to achieve the markers.

As an example, the CT scanner 11 may use the conventional CT scan imaging device to form the CT image. Since the CT technology has been mature, its details will be omitted herein. The image recognizing device 12 is configured to recognize the CT image to check whether or not the object to be inspected has the suspected hazardous articles. It may be achieved by judging whether or not the CT image contains an image feature of the suspected hazardous articles. The image feature of the suspected hazardous articles may include, but not limited to for example special colors (such as black, claybank), shapes, forms (such as liquid, solid powders) of the hazardous articles. The process of the image recognizing device 12 for recognizing the CT image may for example achieved by any suitable known algorithms such as pattern recognition algorithms. If necessary, it may verify whether or not the results of the image recognizing device 12 are correct by means of artificial recognition. The image recognizing device 12 may be implemented by a signal processing device, or may be implemented by a computer or other processors. The image recognizing device 12 may be implemented by a known image recognizer.

As an example, the Raman spectrum measuring device 21 may be implemented by a known Raman spectrum device, which may for example, include a Raman spectroscopic signal sampling device (e.g., including a laser, a lens, a dichroic mirror or an optical filter, and so on) and a spectrometer. The Raman spectrum comparing device 22 may be implemented by a signal processing device, or may be implemented by a computer or other processors. The Raman spectrum comparing device 22 may for example store Raman spectrum data of a plurality of hazardous articles with known compositions. After receiving the Raman spectrum of the suspected hazardous articles measured by the Raman spectrum measuring device 21, it may compare the Raman spectrum with those of the known compositions to determine the composition of the suspected hazardous articles. The Raman spectrum comparing device 22 may decide whether or not the difference between the measured Raman spectrum and the Raman spectra of the known compositions is within a predetermined range so as to determine whether or not the suspected hazardous article has the known composition. It may achieved by calculating a correlation degree between the measured Raman spectroscopic signal and the Raman spectroscopic signals of the known compositions. The above correlation degree may be calculated by various methods. For example, if A(x) represents a Raman spectroscopic signal of a known composition and B(x) represents the measured Raman spectroscopic signal of the suspected hazardous article, in an example, the above correlation degree may be calculated by using the maximum likelihood algorithm on basis of the following equation (1):

$$\text{Corr} = \left(1 - \sqrt{1 - \frac{A(x) \cdot B(x)}{\sqrt{A(x) \cdot A(x)} \sqrt{B(x) \cdot B(x)}}}\right) \times 100\% \quad (1)$$

where Corr is the correlation degree between the Raman spectroscopic signal of the known composition and the measured Raman spectroscopic signal of the suspected hazardous article, and the operator of "·" represents dot product operation.

In another example, A(x) and B(x) may be sampled respectively to obtain their respective n sample points. These sample points are defined as $A_1, A_2, \ldots, A_n$ and $B_1$, $B_2, \ldots, B_n$, respectively. The correlation degree Corr between the Raman spectroscopic signal of the known composition and the measured Raman spectroscopic signal of the suspected hazardous article may be calculated on basis of the following equation (2):

$$\mathrm{Corr} = \frac{\left(\left(A(x) - \frac{\sum_{i=1}^{n} A_i}{n}\right) \cdot \left(B(x) - \frac{\sum_{i=1}^{n} B_i}{n}\right)\right)^2}{\left(\left(A(x) - \frac{\sum_{i=1}^{n} A_i}{n}\right) \cdot \left(A(x) - \frac{\sum_{i=1}^{n} A_i}{n}\right)\right)} \times 100\% \qquad (2)$$
$$\left(\left(B(x) - \frac{\sum_{i=1}^{n} B_i}{n}\right) \cdot \left(B(x) - \frac{\sum_{i=1}^{n} B_i}{n}\right)\right)$$

where the operator of "·" also represents dot product operation.

In another example, A(x) and B(x) may be sampled respectively to obtain their respective n sample points. These sample points are defined as $A_1, A_2, \ldots, A_n$ and $B_1, B_2, \ldots, B_n$, respectively. The correlation degree Corr between the Raman spectroscopic signal of the known composition and the measured Raman spectroscopic signal of the suspected hazardous article may be calculated on basis of the following equation (3):

$$\mathrm{Corr} = \left(1 - \frac{\sum_{i=1}^{n} |A_i - B_i|}{n}\right) \times 100\%. \qquad (3)$$

The above calculations of the correlation degree may be performed for whole Raman spectroscopic signal, or may be performed for local parts with the characterizing portion in the Raman spectroscopic signal. The above paragraphs only give some examples of calculation of the correlation degree. Alternatively, other calculation methods of the correlation degree in the art are also applicable. Determining whether or not the correlation degree between the Raman spectroscopic signal of the known composition and the measured Raman spectroscopic signal of the suspected hazardous article is within a predetermined range may be achieved by determining whether or not the correlation degree exceeds a predetermined threshold. As an example, the threshold for the correlation degree may be such as 0.9, 0.8 or the like.

As an example, in order to decide on whether or not the difference between the measured Raman spectrum of the suspected hazardous article and the Raman spectrum of the known composition is within the predetermined range, alternatively, information on characterizing peaks may be extracted directly by peak intensity detection (amplitude detection) and peak position detection (phase detection or inflection point detection), so as to compare the information of these characterizing peaks in the measured Raman spectrum of the suspected hazardous article with those in the Raman spectrum of the known composition. In this case, the predetermined range may be a threshold of difference between the positions of the corresponding characterizing peaks in the measured Raman spectrum of the suspected hazardous article and in the Raman spectrum of the known composition (for example, the threshold may be in a range of 10 to 50 wave numbers) or a threshold of difference between peak intensities of the characterizing peaks.

In an example, the security inspection apparatus 100 may further include an information recording device 30. The information recording device 30 is arranged to record the marker recognized by the object marker recognizing device 23 and the CT image of the object which has the predetermined marker (acquired by the CT inspection device 10) and the composition of the suspected hazardous article (acquired by the Raman spectrum inspection device 20) in the object. It may associate the object (for example luggage packs), the suspected hazardous article, the inspection results of the CT inspection device 10 and the inspection results of the Raman spectrum inspection device 20 with each other clearly, such that the source of the hazardous article can be found more easily. The information recording device 30 may for example include a computer, a server, an optical disc recording device, a hard disk recording device, or the like.

As an example, the image recognizing device 12 and the Raman spectrum comparing device 22 may be two components separated from each other, or may be integrated with each other, for example may be used as two modules of one signal processing device. As an example, the image recognizing device 12 and the Raman spectrum comparing device 22 may be integrated with the information recording device 30.

In an example, the security inspection apparatus may further include one or more video capture devices 40, 50. The video capture devices 40, 50 are arranged to capture videos of the object and a person carrying the object. It provides additional information for the security inspection. As an example, the marker, the CT image, the videos and the composition of the suspected hazardous article for a same object to be inspected may be recorded in association. So-called "recorded in association" means that when recorded, a clear mapping relation (e.g., one-to-one correspondence) among the marker, the CT image, the videos and the composition of the suspected hazardous article for the same object to be inspected is established, such that when any term of the above information is read, other information of the same object may also be acquired. For example, the information of the same object may be recorded in a same association list in a database of the information recording device 30. In this way, once the security inspection device 100 finds that the object has the suspected hazardous article, it may determine the source of the suspected hazardous article rapidly from the videos of the object and the person carrying the object.

Figure 2:
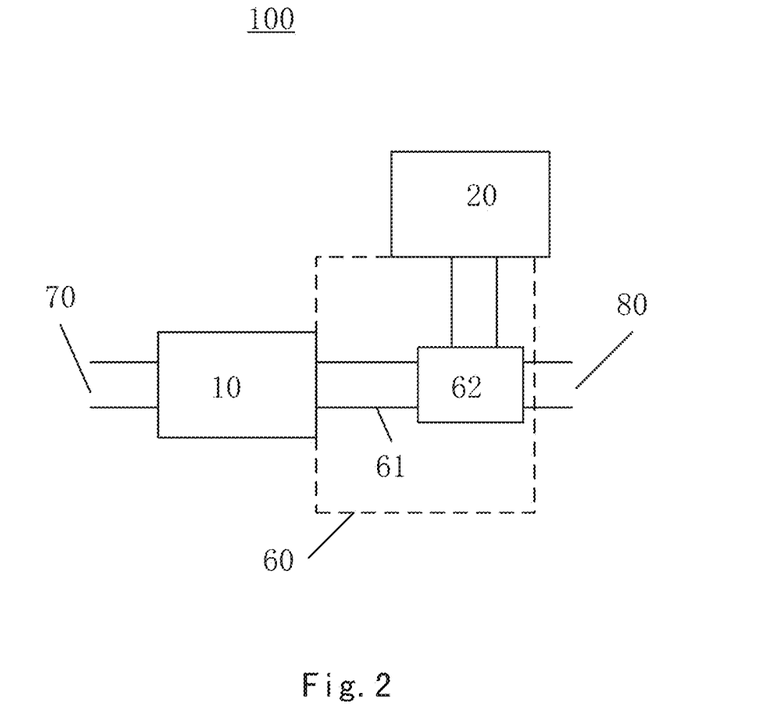
FIG. 2 is a schematic view showing an arrangement for an object to be inspected on a transmission device in the security inspection apparatus according to an embodiment of the disclosed technology.

In an example, the security inspection apparatus 100 may further include an object transmission device 60 located between the CT inspection device 10 and the Raman spectrum inspection device 20. The object transmission device 60 has a transporting device 61 configured to transport the object to the Raman spectrum inspection device 20 from the CT inspection device 10. The transporting device 61 is provided with a filtering device 62 configured to recognize the marker on the object to transport the object having the marker to the Raman spectrum inspection device 20 while transporting the object which has not the marker out of the security inspection apparatus 100. As shown in FIG. 2, the object may be transported into the CT inspection device 10 from an inlet 70 of the security inspection apparatus 100. After being inspected by the CT inspection device 10, the object is transported by the transporting device 61 to the filtering device 62. The filtering device 62 can inspect whether or not a predetermined marker made by the object marking device 13 (for example, a two dimensional code generator) is present on the object. If the predetermined marker is present, the object will be allowed to be transported by the transporting device 61 towards the Raman spectrum inspection device 20; otherwise, if the predetermined marker is not present, the object will be transported to an outlet 80 of the security inspection device 100. The transporting device 61 may for example be implemented by components such as a transmission belt, a track or the like. The filtering device 62 may for example be formed by a marker recognizing device (for example, a two dimensional code recognizing device or the like) and a diverter (for example rollers, robots or the like for changing the transmission direction of the object). By means of the object transmission device 60, it may correctly determine which objects should be transported to the Raman spectrum inspection device 20 to avoid occurrence of inspection errors.

An embodiment of the present application also provides a security inspection method including the following steps:

S10: scanning an object to be inspected by using a CT scanner to generate a CT image and check whether or not the object has a suspected hazardous article;

S20: making a predetermined marker on the object having the suspected hazardous article;

S30: recognizing the predetermined marker on the object; and

S40: extracting the Raman spectrum of the suspected hazardous article in the object which has the predetermined marker and comparing the Raman spectrum of the suspected hazardous article with Raman spectra of known compositions to determine a composition of the suspected hazardous article.

By means of the above security inspection method, it may achieve double inspection, i.e., the CT scanning inspection and the Raman spectrum inspection, so that not only may achieve the ray fluoroscopy inspection of the object (for example, luggage packs or the like), but also may determine the composition of the suspected hazardous article in the object. It should be noted that sequences of the above steps S30 and S40 may be inverted, or may be performed simultaneously.

Figure 3:
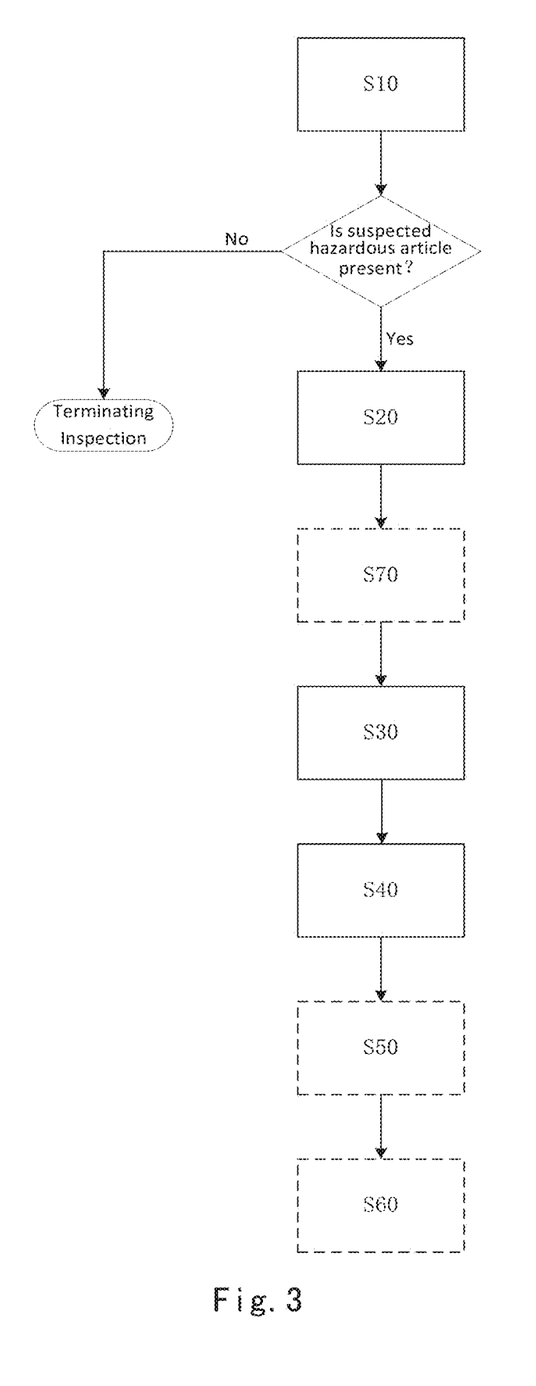
FIG. 3 is a flow chart showing a security inspection method according to an embodiment of the disclosed technology.

As shown in FIG. 3, if it is determined that the object has the suspected hazardous article in the Step S10, the inspection flow may be terminated.

In an example, the security inspection method may further include:

Step S50: recording the recognized marker and the CT image of the object which has the predetermined marker and inspection results (e.g., the composition of the suspected hazardous article) obtained by the Raman spectrum measuring device.

As an example, the security inspection method may further include:

Step S60: capturing videos of the object and a person carrying the object and recording the videos of the object which has the predetermined marker and the person carrying the object, the CT image of the object which has the predetermined marker and the composition of the suspected hazardous article in association.

As an example, the marker is a two dimensional code. For example, the two dimensional code may be generated by a two dimensional code generator. In an example, a two dimensional code label may be pasted onto the object. Meanwhile, in the database, the CT image may be labelled with information of the two dimensional code. In another example, if the two dimensional code has been provided on the external packing of the object (or the suspected hazardous article), the information may be scanned by the two dimensional code generator and the corresponding CT image is labelled. In another example, two labels of two dimensional codes may also be generated and labelled for example on the object and on the packing of the object respectively.

As an example, between the step S20 and the step S40, the security inspection method may further include:

Step S70: recognizing the marker on the object and transporting the object which has the marker to the Raman spectrum inspection device to perform the Step S40 while transporting the object which has not the marker out of the security inspection apparatus.

As an example, the security inspection apparatus 100 may further include a controller configured to control parts such as the CT scanner 11, the image recognizing device 12, the object marking device 13, the Raman spectrum measuring device 21, the Raman spectrum comparing device 22, the object marker recognizing device 23 and the like to achieve the above security inspection method. In an example, the image recognizing device 12 and the Raman spectrum comparing device 22 may be integrated with the controller.

In the embodiments of the present application, the suspected hazardous article may include but not limited to any substances such as liquid substances, solid powders, other types of solid or sol-gel.

Figure 4:
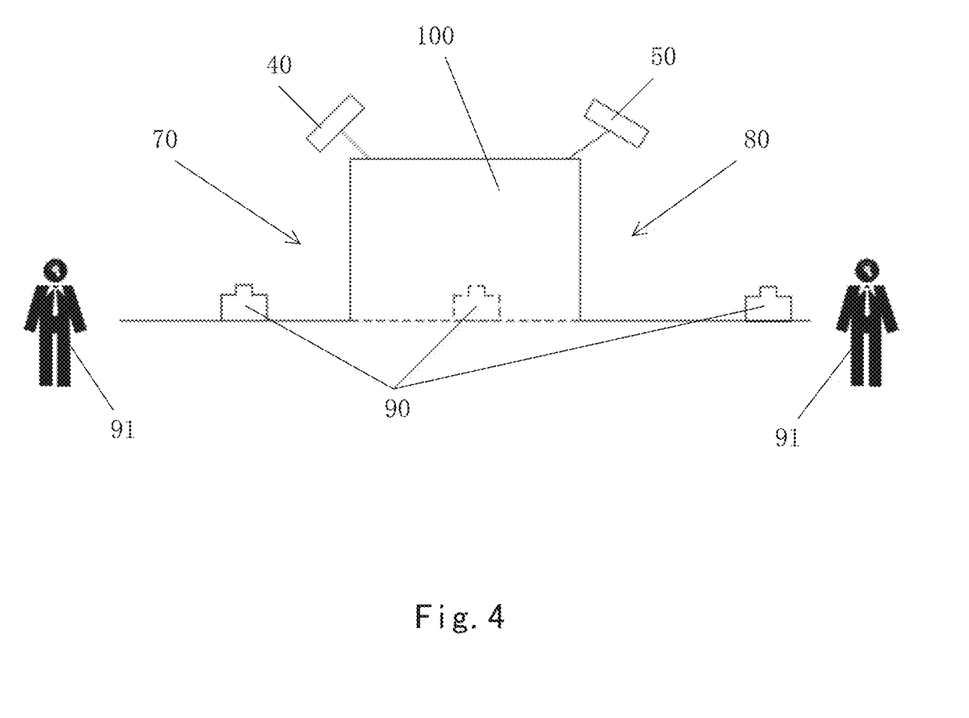
FIG. 4 is a schematic view showing a security inspection apparatus according to an embodiment of the disclosed technology in operation of inspecting luggage articles.

FIG. 4 shows exemplified applications of the security inspection apparatus according to an embodiment of the disclosed technology in inspection of luggage packs. In the example, a person 91 (for example a passenger) carrying the object 90 to be inspected puts the object 90 (for example a luggage pack) into the security inspection apparatus 100 from the inlet 70 of the security inspection apparatus 100 for inspection (the inspection is performed specifically by the CT inspection device 10 and the Raman spectrum inspection device 20). If the object has passed through the inspection successfully, the object 90 will be transported out of the outlet 80 of the security inspection apparatus 100 and the flow of security inspection is finished. During inspection, as an example, before the object 90 is inspected by using the Raman spectrum inspection device 20, the packs may be opened manually or by robots to expose the suspected hazardous article for convenience of inspection. In order to further improve the inspection efficiency, for example, when the object 90 is inspected by the CT inspection device 10, the position of the suspected hazardous article may also be marked in the CT image, so as to inspect it by the Raman spectrum inspection device 20 more conveniently in subsequent stages. In the example shown in FIG. 4, a video capture device (for example a camera) 40 is provided at the inlet 70 of the security inspection apparatus 100 and another video capture device (for example a camera) 50 is also provided at the outlet 80 of the security inspection apparatus 100. These video capture devices 40, 50 may be configured to shoot the videos of the object 90 to be inspected and the videos of the person 91 carrying the object 90 at the inlet 70 and at the outlet 80. As an example, the video capture device for shooting the videos of the object 90 may be different from that for shooting the videos of the person 91 carrying the object 90, to optimize the resolution and shooting positions respectively.

The above description has explained various embodiments of the above security inspection apparatus by schematic views, flow charts and/or examples. In case that the schematic views, flow charts and/or examples each include one or more functions and/or operations, the skilled person in the art should understand that each function and/or operation in such schematic views, flow charts and/or examples may be implemented separately and/or collectively by various structures, hardware, software, firmware or any combination of them in essential. In an embodiment, some parts of the subject of the embodiment of the present application may be implemented by Application Specific Integrated Circuits (ASIC), Field Programmable Gate Arrays (FPGA), Digital Signal Processors (DSP) or other integrated forms. However, the skilled person in the art should understand that some aspects of the embodiments disclosed herein may be implemented equally in the integrated circuit entirely or partly, implemented as one or more computer program running on one or more computer (for example, implemented as one or more program running on one or more computer system), implemented as firmware, or implemented as any combination of the above methods in essential. From the disclosed technology, the skilled person in the art has capability of designing circuits and/or writing software and/or firmware codes. Furthermore, the skilled person in the art will appreciate that the mechanism of the subject of the disclosed technology may be delivered as various forms of program products and the exemplified embodiments of the subject of the disclosed technology may be applicable independent of the specific types of the signal carrying media that perform the delivery in practice. Examples of the signal carrying media include, but not limited to: recordable media, such as a floppy disc, a hard disk drive, an optical disc (CD, DVD), a digital magnetic tape, a computer memory or the like; and transmission media such as digital and/or analogue communication media (for example, an optical fiber cable, a wave guide, a wired communication link, a wireless communication link or the like).

Although the disclosed technology has been explained with reference to the drawings, the embodiments shown in the drawings are only illustrative, instead of limiting the present application.

Although some embodiments of the general inventive concept are illustrated and explained, it would be appreciated by those skilled in the art that modifications and variations may be made in these embodiments without departing from the principles and spirit of the general inventive concept of the application, the scope of which is defined in the appended claims and their equivalents.

The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. A security inspection apparatus, comprising:
a CT inspection device and a Raman spectrum inspection device, wherein the CT inspection device comprises:
a CT scanner arranged to scan an object to be inspected and to generate a CT image;
an image recognizing device arranged to recognize the CT image so as to check whether or not the object has a suspected hazardous article; and
an object marking device arranged to place a predetermined marker on the object which has the suspected hazardous article; and
wherein the Raman spectrum inspection device comprises:
a Raman spectrum measuring device arranged to extract a Raman spectrum of the suspected hazardous article in the object,
a Raman spectrum comparing device arranged to compare the Raman spectrum of the suspected hazardous article with Raman spectra of known compositions to determine a composition of the suspected hazardous article, and
an object marker recognizing device arranged to recognize the predetermined marker on the object.

2. The security inspection apparatus of claim 1, further comprising:
an information recording device arranged to record the marker recognized by the object marker recognizing device and the CT image of the object which has the predetermined marker and the composition of the suspected hazardous article in the object.

3. The security inspection apparatus of claim 2, wherein the object marking device is a two dimensional code generator, and the marker is a two dimensional code, and the object marker recognizing device is a two dimensional code recognizing device.

4. The security inspection apparatus of claim 3, further comprising an object transmission device located between the CT inspection device and the Raman spectrum inspection device, the object transmission device having a transporting device configured to transport the object to the Raman spectrum inspection device from the CT inspection device,
wherein the transporting device is provided with a filtering device configured to recognize the marker on the object to transport the object having the marker to the Raman spectrum inspection device while transporting the object which has not the marker out of the security inspection apparatus.

5. The security inspection apparatus of claim 3, further comprising a video capture device arranged to capture videos of the object and a person carrying the object.

6. The security inspection apparatus of claim 5, wherein the marker, the CT image, the videos and the composition of the suspected hazardous article for a same object to be inspected are recorded in association.

7. The security inspection apparatus of claim 2, further comprising a video capture device arranged to capture videos of the object and a person carrying the object.

8. The security inspection apparatus of claim 7, wherein the marker, the CT image, the videos and the composition of the suspected hazardous article for a same object to be inspected are recorded in association.

9. The security inspection apparatus of claim 2, further comprising an object transmission device located between the CT inspection device and the Raman spectrum inspection device, the object transmission device having a transporting device configured to transport the object to the Raman spectrum inspection device from the CT inspection device,
wherein the transporting device is provided with a filtering device configured to recognize the marker on the object to transport the object having the marker to the Raman spectrum inspection device while transporting the object which has not the marker out of the security inspection apparatus.

10. The security inspection apparatus of claim 1, further comprising an object transmission device located between the CT inspection device and the Raman spectrum inspection device, the object transmission device having a transporting device configured to transport the object to the Raman spectrum inspection device from the CT inspection device,
wherein the transporting device is provided with a filtering device configured to recognize the marker on the object to transport the object having the marker to the Raman spectrum inspection device while transporting the object which has not the marker out of the security inspection apparatus.

11. A security inspection method comprising:
scanning an object to be inspected by using a CT scanner to generate a CT image and checking whether or not the object has a suspected hazardous article;
making a predetermined marker on the object having the suspected hazardous article;
recognizing the predetermined marker on the object; and
extracting a Raman spectrum of the suspected hazardous article in the object which has the predetermined marker and comparing the Raman spectrum of the suspected hazardous article with Raman spectra of known compositions to determine a composition of the suspected hazardous article.

12. The security inspection method of claim 11, further comprising:
recording the recognized marker and the CT image of the object which has the predetermined marker and the composition of the suspected hazardous article determined by a Raman spectrum inspection device.

13. The security inspection method of claim 12, wherein the marker is a two dimensional code.

14. The security inspection method of claim 12, further comprising capturing videos of the object and a person carrying the object and recording, in association, the videos of the object which has the predetermined marker and the person carrying the object, with the CT image of the object which has the predetermined marker and the composition of the suspected hazardous article in association.

15. The security inspection method of claim 14, wherein the marker is a two dimensional code.

16. The security inspection method of claim 11, wherein the marker is a two dimensional code.

* * * * *